United States Patent [19]

Huber

[11] Patent Number: 5,098,658
[45] Date of Patent: Mar. 24, 1992

[54] DEVICE FOR ANALYZING SAMPLES FOR MERCURY AND/OR HYDRIDE-FORMING ELEMENTS

[75] Inventor: Bernhard Huber, Überlingen, Fed. Rep. of Germany

[73] Assignee: Bodenseewerk Perkin Elmer GmbH, Überlingen, Fed. Rep. of Germany

[21] Appl. No.: 526,090

[22] Filed: May 21, 1990

[30] Foreign Application Priority Data

Jun. 2, 1989 [DE] Fed. Rep. of Germany ....... 3917956

[51] Int. Cl.$^5$ ............................................. C01G 13/00
[52] U.S. Cl. ...................................... 422/78; 422/83; 422/91; 436/81
[58] Field of Search ............... 422/83, 78, 91; 436/81, 436/155, 171, 177

[56] References Cited

U.S. PATENT DOCUMENTS

| | | | |
|---|---|---|---|
| 3,711,248 | 1/1973 | Coffey | 436/81 |
| 3,713,776 | 1/1973 | Capuano | 422/91 |
| 3,826,614 | 7/1974 | Capuano | 436/81 |
| 3,826,618 | 7/1974 | Capuano | 422/91 |
| 3,844,719 | 10/1974 | Hammitt | 422/78 |
| 3,884,639 | 5/1975 | Sugiyama | 436/81 |
| 4,023,929 | 5/1977 | Becker et al. | 422/78 |
| 4,404,288 | 9/1983 | Huber | 422/78 |
| 4,758,519 | 7/1988 | Nakao et al. | 422/83 |

Primary Examiner—Robert J. Warden
Assistant Examiner—Theresa A. Trembley
Attorney, Agent, or Firm—Edwin T. Grimes

[57] ABSTRACT

In a device for analyzing samples for mercury and/or hydride-forming elements by means of atomic absorption spectroscopy, a first arrangement for determining the mercury according to the amalgam method comprising passage throttling means in the form of a washing bottle and a tube connected downstream to a reaction vessel, the other end of which tube is connected to the measuring cell. The tube contains a gold net adapted to be heated and recooled according to the amalgam method. The second arrangement by which hydrides of the sample are directly connected to the measuring cell employs a conduit which leads directly to the measuring cell, bypassing the gold net by branching off from between the reaction vessel and washing bottle. The tube is connectable to a carrier gas source between the washing bottle and position of the gold net in the tube through a first shut-off valve. A second shut-off valve is arranged in the conduit directly leading to the measuring cell. The first and the second shut-off valves are interconnected so that opening the first shut-off valve causes the second shut-off valve to close.

3 Claims, 1 Drawing Sheet

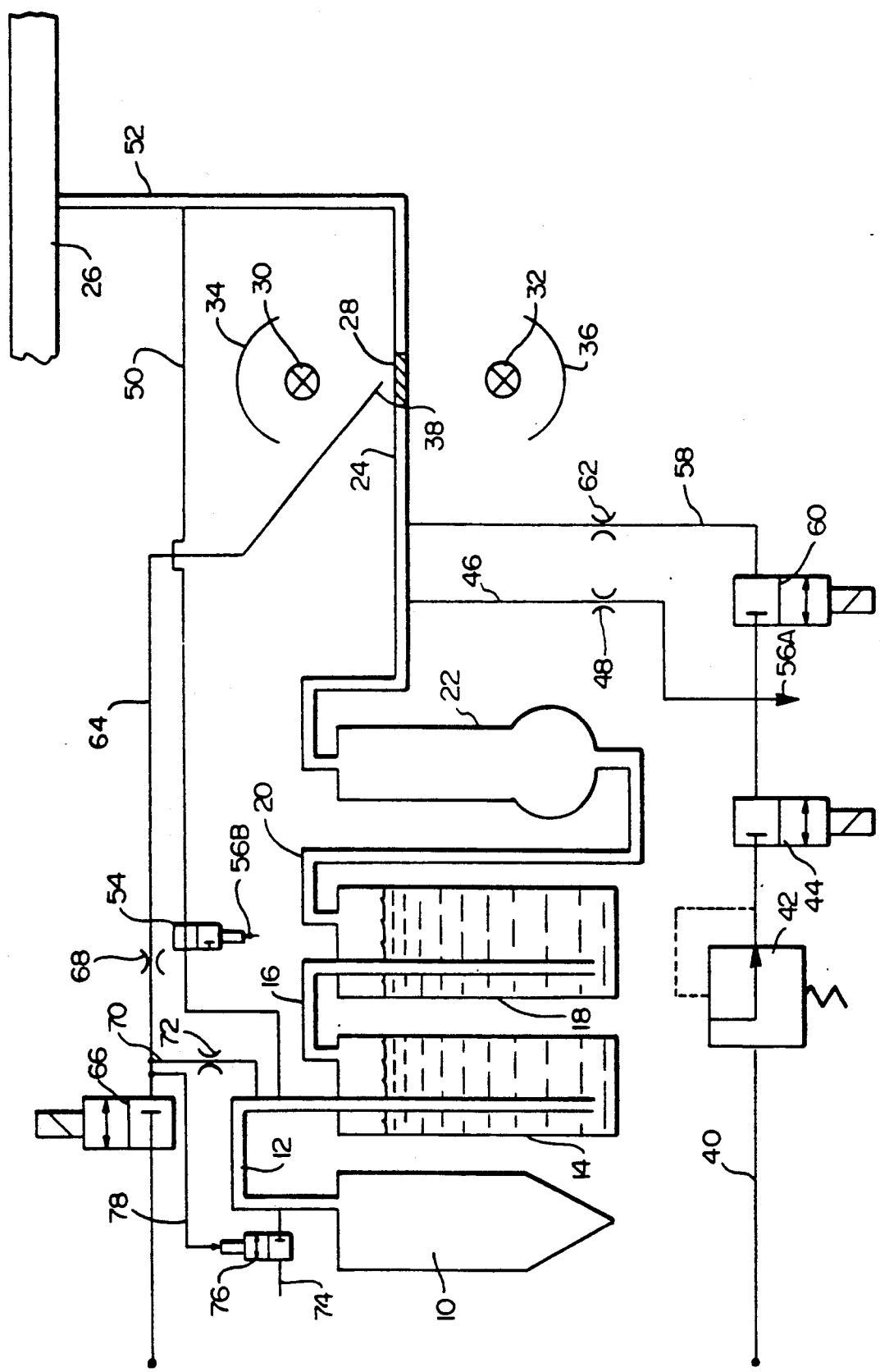

DEVICE FOR ANALYZING SAMPLES FOR MERCURY AND/OR HYDRIDE-FORMING ELEMENTS

TECHNICAL FIELD

The invention relates to a device for analyzing samples for mercury and/or hydride-forming elements by means of atomic absorption spectroscopy, having a reaction vessel, into which the sample, together with a reagent, is introduced, and a tubular measuring cell, connected to the reaction vessel through a conduit with the measuring light beam of an atomic absorption spectrometer being adapted to pass through this measuring cell.

It is necessary to determine the concentration of a looked for element in a sample. To this end, in atomic absorption spectroscopy, an "atomic cloud" is generated in which the looked for element is present in atomic state. A measuring light beam from a line-emitting light source passes through this atomic cloud, which measuring light beam comprises the resonant lines of the looked for element. This measuring light beam is specifically absorbed by the atoms of the looked for element. The attenuation of the measuring light beam is thus a measure of the quantity of atoms of the looked for element in the atomic cloud.

A method of atomizing the looked for element in the sample consists in generating a volatile hydride of the looked for element by adding a reagent. This hydride is then decomposed in a heated measuring cell through which the measuring light beam passes. Then, the looked for element appears in the measuring cell in atomic state.

Similarly, the amalgam method may be used wherein mercury is expelled from a sample and transmitted into the measuring cell by a carrier gas flow.

The invention relates to a device for determining hydride-forming elements and mercury according to this method.

BACKGROUND ART

Devices in which a reagent is added to a sample in a reaction vessel, and the thus-obtained gaseous measuring sample, e.g., a volatile hydride of a looked for element, is transmitted into a heatable measuring cell, are known in different forms. Examples of such devices are DE-PS 26 27 255, DE-PS 26 40 285, DE-AS 27 18 381, DE-OS 27 29 744, and DE-AS 27 35 281. Further devices of this type are shown in DE-AS 28 51 058, DE-PS 27 48 685, DE-PS 32 26 234, and DE-PS 32 26 235. DE-OS 35 25 166 shows an arrangement in which volatile hydrides are supplied to a plasma emission device or to a measuring cell wherein, by means of the sample and reagent pumps, the sample and the reagent can be alternatively rapidly united or continual liquid currents can be generated over a relatively long measuring period of time by the continuous operation with slow forward displacement of the pump pistons.

DE-AS 29 43 092 describes, with regard to the prior art, a method by which mercury is expelled from a sample by means of a reducing agent. For determining small quantities of mercury, the mercury vapor obtained by the reduction is guided for enrichment over silver or gold wool. Thereby, the mercury forms an amalgam with the silver and the gold, respectively. The mercury, thus bound as amalgam, can then be re-expelled through heating and guided into a measuring cell. A higher concentration of mercury is thus obtained in the measuring cell than would be obtained with the direct measurement of the mercury vapor expelled by the reducing agent from the sample solution. Thus, the sensitivity can be increased by approximately the factor 10.

According to the teachings of DE-AS 29 43 092, the mercury is not separated by expelling mercury vapor from a sample solution by means of a reducing agent but rather by the electrolysis of the sample solution.

DE-OS 37 23 178 shows a flow injection device wherein a flow of reagent to a measuring device is generated by means of a peristaltic pump. Through a reversing valve having a loop of tubing located in a conduit of a carrier liquid, a sample liquid contained in the look of tubing is introduced into the flow of reagent. The reagent is a reducing agent which produces, out of hydridizing components of the sample liquid such as arsenic, corresponding volatile hydrides which are separated from the liquid flow in a gas separator and guided into a heated measuring cell. The gas separator forms herein the "reaction vessel".

German Published Patent Application No. 3,344,914 describes an apparatus for analyzing a liquid containing constituents which form volatile compounds, by means of a physical analyzing device. A reaction vessel comprises at its lower end, an outlet valve. A flushing valve which is connected to a flushing liquid reservoir is located at the upper end of the reaction vessel. A metering conduit provided with an inlet valve opens into the lower half of the reaction vessel. Via the metering conduit, sample liquid is conveyed from sample receptacles into the reaction vessel by means of a peristaltic pump. The sample receptacles are present on a turntable. The valves are controlled by programmed control means in a manner such that, following each analysis, the reaction vessel is emptied and then flushed using the flushing liquid; thereafter, a further sample is supplied and reagent is added thereto.

PCT Published Application No. WO 88/08527 describes a graphite tube furnace for atomizing liquid samples. A liquid sample is introduced into a graphite tube through an inlet opening. Atomization is effected by passing a strong electric current through the graphite tube. During this operation, an inert gas flow is flown past the graphite tube. Means are provided for infeeding reactive gases into the chamber defined by the graphite tube. In this manner, reducing, oxidizing, or neutral environmental conditions can be created within the chamber, or there can also be varied the pH-value.

In the textbook entitled "Atomic Absorption Spectrometry", by Welz, published by Verlag Chemie 1983, pages 71 to 84, there are described analytical methods of producing volatile hydrides from liquid samples by the addition of reagents. It is described in which manner these hydrides are then atomized and the process can be automated.

A publication by Mertens and Althaus in "Fresenius Zeitschrift für analytische Chemie", vol. 316, 1983, pages 696 to 698, describes a method of determining mercury by means of the amalgam technique, using hydroxylammonium chloride and sodium borohydride or tin (II) chloride. Also in this method, a reducing agent is added to a liquid sample in a reaction vessel. The thus formed mercury vapor is flushed by means of a nitrogen current through a wash flask and an aerosol trap and flows over a gold platinum wire. The mercury is enriched thereat by amalgam formation. The enriched mercury is driven off by the application of heat and determined in a measuring cuvette by atomic absorption spectroscopy.

A publication by Messerschmidt and Tolg in "Fresenius Zeitschrift fur analytische Chemie", vol. 327, 1987, pages 233 to 234, describes the determination of selenium. Therefore, selenium, which is present in a liquid sample, is converted into a volatile hydride by sodium borohydride and passed through an adsorption tube by means of a helium current. The adsorption tube can be cooled by liquid nitrogen whereby selenium hydride is adsorbed at an adsorbent. After such enrichment, the selenium hydride can be driven off by rapidly heating the adsorption tube and passed into the measuring cuvette of an atomic absorption spectrometer.

Austrian Patent No. 350,508 relates to a method of quantitatively determining mercury in organic materials. A reagent is infed into a reaction vessel containing the sample by means of a peristaltic pump. Also, a carrier gas stream is infed into this reaction vessel. The thus formed mercury vapor is passed to an adsorption tube via a drying tube. Therein, the mercury is enriched and ultimately driven off by heating the adsorption tube and passed to a measuring cuvette.

German Published Patent Application No. 3,044,627 relates to an apparatus for infeeding samples into a graphite tube for flameless atomic absorption spectroscopy. A sample is applied to a crucible-shaped sample carrier which can be introduced into the graphite tube. This sample carrier is subject to contactless heating for drying and ashing the sample by heating means disposed exterior of the sample carrier.

DISCLOSURE OF INVENTION

It is the object of the invention to create an apparatus which permits, without the need for alternative rebuilding the analysis of hydride-forming elements, a direct analysis of mercury without enrichment, or an analysis of mercury with enrichment of the mercury amalgam.

According to this invention, this object is achieved in that for determining the mercury according to the amalgam method, passage throttling means and a tube are connected downstream to the reaction vessel, which tube is connected to the measuring cell and in which is an amalgam-forming body adapted to be heated and recooled and having a large surface, a conduit branches off between the reaction vessel and passage throttling means, which conduit leads directly to the measuring cell, bypassing the amalgam-forming body, the tube between the passage throttling means and the amalgam-forming body are arranged to be connected to a carrier gas source through a first shut-off valve, a second shut-off valve is arranged in the conduit which leads directly to the measuring cell, and the first and the second shut-off valve are interlocked such that, when opening the first shut-off valve, the second shut-off valve closes.

When the first shut-off valve is closed, the second shut-off valve is open. The gas emerging from the reaction vessel (gas separator) then flows through the second shut-off valve and through the associated conduit directly into the measuring cell. The passage throttling means controls the amount of gas current to the tube with the gold net. This is the mode of operation when analyzing conventional hydride-forming elements or when directly measuring mercury without enrichment. When the first shut-off valve opens, the second shut-off valve is closed. The gas current must now flow through the passage throttling means over the gold net. The gold net is relatively cool such that mercury enriches as amalgam on the gold net. By heating the gold net, the mercury is then set free such that it is transported by the carrier gas current gaseously with an increased concentration to the measuring cell. A rebuilding of the apparatus is not required for the changeover from one mode of operation to the other.

BRIEF DESCRIPTION OF THE DRAWINGS

FIG. 1 illustrates in schematic form an embodiment of the present invention.

DESCRIPTION

In FIG. 1, a gas separator is designated by 10. The gas separator 10 forms a reaction vessel in which volatile hydrides or mercury, expelled by a reducing agent from a sample liquid, separate from the sample liquid, and out of which these gases or vapors flow through an outlet conduit 12. The gas separator 10 forms part of a flow injection device, as illustrated and described in the above-mentioned DE-OS 37 23 178.

The outlet conduit 12 is guided into a first washing bottle 14 up to the vicinity of the bottom of this washing bottle 14. An outlet conduit 16 extends from the upper side of the tightly closed washing bottle 14 and is guided into a second washing bottle up to the vicinity of the bottom of this second washing bottle 18. An outlet conduit 20 extends from the upper side of the tightly closed second washing bottle 18 and is guided to one end of a drying tube 22. A tube 24 extends from the other end of the drying tube 22. The tube 24 is guided to a measuring cell 26.

A gold net 28 is located as the amalgam-forming body of a large surface in the tube 24. The gold net 28 can be heated by lamps 30,32 with reflectors 34,36. The tube 24 is a quartz tube. The heating radiation of the lamps 30 and 32 can thus pass largely non-attenuated through the wall of the tube and can be absorbed by the gold net. The tube 24 and the gold net 28 can rapidly be recooled by a compressed air current of a compressed air outlet 38 after heating and after the lamps 30 and 32 are switched off.

An inert carrier gas, such as argon, is supplied through a carrier gas conduit 40. The pressure of the carrier gas is regulated by a pressure regulator 42. A first shut-off valve 44 is located in the carrier gas conduit 40 upstream to the pressure regulator. The first shut-off valve 44 is a magnet valve. The first shut-off valve is controlled by a microcomputer of the atomic absorption spectrometer.

The first branch conduit 46 extends from the carrier gas conduit 40 behind the first shut-off valve 44. The first branch conduit 46 opens into the tube 24 upstream to the gold net 28, i.e., between the drying tube 22 and the gold net 28. A throttle 48 is provided in the branch conduit 46. The throttle 48 is designed such that a relatively small carrier gas flow of about 75 milliliters per minute flows through the branch conduit 46 when the first shut-off valve 44 is open.

A first conduit 50 extends from the outlet conduit 12 between the reaction vessel 10 and washing bottle 14. The conduit 50 leads directly to the measuring cell 26, bypassing the washing bottles 14,18, the drying tube 22, and the gold net 28. In the illustrated preferred embodiment, the conduit 50 opens in a perpendicular end portion 52 of the tube 24 close in front of its opening into the central portion of the measuring cell 26. A second shut-off vessel 54 is arranged in the conduit 50. The second shut-off vessel 54 is locked with the first shut-off valve 44 such that the second shut-off valve 54 opens when the first shut-off valve 44 is closed, and the second shut-off valve 54 closes when the first shut-off valve 44 is open. This is achieved in that the second shut-off valve 54 is a pneumatically controlled valve adapted to be controlled to be closed by the pressure downstream to the first shut-off valve 44 through a connection 56A,56B against an opposing force. When the first shut-off valve 44 opens, the pressure of the carrier gas acts onto the second shut-off valve 54 and presses the second shut-off valve 54 into the closed position.

The gas which is separated from the sample and reagent liquid in the reaction vessel 10 then flows through a part of the outlet conduit 12 and through the conduit 50 directly to the measuring cell 26. The washing bottle 14 herein represents a barrier which prevents this gas from passing through the washing bottles 14,18 and the drying tube 22 and through the gold net 28.

A second branch conduit 58 branches off from the carrier gas conduit 40 downstream to the first shut-off valve 44 and parallel to the first branch conduit 46. A third shut-off valve 60 and a flow throttle 62 are arranged in the second branch conduit 58. The flow throttle 62 is so designed that when the shut-off valves 44 and 60 are open, a carrier gas current flows through the second branch conduit, which carrier gas current is considerably greater than the carrier gas current in the first branch conduit 46. The carrier gas current in the second branch conduit 58 is approximately 1,000 milliliters per minute.

The gold net 28 and the tube 24 can be cooled by a compressed air current emerging from the compressed air outlet 38. The compressed air outlet 38 is connected to a compressed air conduit 64. A fourth shut-off valve 66 is arranged in the compressed air conduit 64. A flow throttle 68 is located downstream to the fourth shut-off valve 66 and the flow throttle 68. The rinsing conduit 70 is guided to the outlet conduit 12 of the reaction vessel 10 closely upstream to the washing bottle 14. The rinsing conduit 70 comprises a flow throttle 72. The outlet conduit 12 is connectable through an outlet 74 to the atmosphere closely behind the reaction vessel 10. The outlet 74 is controlled by a fifth shut-off valve 76. The fifth shut-off valve 76 is locked with the fourth shut-off valve 66 such that the fifth shut-off valve opens when the fourth shut-off valve opens. To this end, the fifth shut-off valve 76 is formed as a pneumatically controlled valve. The fifth shut-off valve 76 is connected to the compressed air conduit 64 upstream to the fourth shut-off valve 66 through a control conduit 78. When the fourth shut-off valve 66 opens, the pressure in the compressed air conduit 64 upstream to the flow throttle 68 presses the fifth shut-off valve 76 against an opposing force into the open position.

The described arrangement operates as follows:

When analyzing a hydride-forming element, the first shut-off valve 44 remains closed. Thereby, the connection 56A,56B is depressurized and the pneumatically controlled second shut-off valve 54 is open. The hydrogen and the hydrides separated in the reaction vessel 10 flow through the conduit 50 directly to the measuring cell. A flow to the gold net 28 is prevented by the water column in the washing bottle 14.

If an analysis for mercury shall be effected wherein the mercury is enriched according to the amalgam method, the first shut-off valve 44 formed as magnet valve is opened by the microcomputer of the atomic absorption spectrometer.

Therewith, pressure is exerted onto the connection 56A,56B and the pneumatically controlled second shut-off valve 54 is closed. The gas (mercury vapor) deposited in the reaction vessel 10 must now flow through the washing bottles 14 and 18 and through the drying tube 22 as well as the tube 24. The gas flows over the gold net 28. The gold net 28 is heated and is cooled down by an analysis which may be performed ahead of time in a way described below. Thus, the mercury is bound as amalgam and enriched on the surface of the gold net 28. When a sufficient enrichment of the mercury is obtained, the gold net is heated by switching on the lamps 30,32. The amalgam is decomposed by the heating and the mercury is transported by the relatively weak carrier gas flow flowing through the first branch conduit to the measuring cell 26. Therewith, an increase in the concentration by approximately a factor of ten and a correspondingly increased measuring signal results as compared to a direct introduction of the mercury vapor into the measuring cell 26. Furthermore, the influence of interfering, other components in the sample, is reduced.

After the measurement, the third shut-off valve is opened. The third shut-off valve 60 is also formed as magnet valve and is controlled by the microcomputer of the atomic absorption spectrometer. By opening the third shut-off valve 60, an increased carrier gas flow is guided through the tube 24 through the second branch conduit 58. Thereby, the tube 24 is rinsed.

The lamps 30 and 32 are switched off. Then, the fourth shut-off valve 66 opens. A compressed air jet from the compressed air outlet 38 is directed against the tube 24 in the area of the gold net 28 and rapidly cools down the tube 24 and the gold net 28 such that, after a short period of time, the apparatus is already available for the next analysis with a cool gold net 28. By opening the fourth shut-off valve 66, the fifth shut-off valve 76 is also pressed open through the control conduit 78. Compressed air is blown through the rinsing conduit into the outlet conduit 12 and through the outlet 74 into the atmosphere. This compressed air current presses drops, which may collect in the outlet conduit 12, back into the reaction vessel 10, i.e., the gas separator.

I claim:

1. An apparatus for analyzing samples for mercury and/or hydride-forming elements directly or by the amalgam method by means of atomic absorption spectroscopy, comprising
   a reaction vessel for receiving a sample together with a reagent,
   a measuring cell,
   a tube connecting said reaction vessel to said measuring cell,
   an amalgam-forming body disposed in said tube adapted to be heated and recooled,
   a conduit connecting said reaction vessel to said measuring cell bypassing said amalgam-forming body,
   a source of carrier gas,
   a first shut-off valve connecting said source of carrier gas to said tube upstream of said amalgam-forming body, a second shut-off valve disposed in said conduit pneumatically controlled and arranged to be moved from its normally open to closed position by carrier gas pressure downstream to said first shut-off valve, said first and second shut-off valves being interlocked such that, when said first shut-off valve is opened, said second shut-off valve is closed, a washing bottle and a drying tube connecting said reaction vessel to said tube containing the amalgam-forming body, said washing bottle forming a passage throttling means to said reaction vessel, a first branch conduit connecting said first shut-off valve to said tube, a second branch conduit parallel to said first branch conduit connecting said first shut-off valve to said tube, a third shut-off valve disposed in said second branch conduit, first and second flow resistance disposed in each of said first and second branch conduits, respectively.

said first flow resistance having a substantially higher resistance to flow than said second flow resistance.

2. An apparatus for analyzing mercury and/or hydride-forming elements directly or by the amalgam method by means of atomic absorption spectroscopy, comprising a reaction vessel for receiving sample together with a reagent, a measuring cell, a tube connecting said reaction vessel to said measuring cell, an amalgam-forming body disposed in said tube adapted to be heated and recooled, a conduit connecting said reaction vessel to said measuring cell bypassing said amalgam-forming body, a source of carrier gas, a first shut-off valve connecting said source of carrier gas to said tube upstream of said amalgam-forming body, a second shut-off valve disposed in said conduit, said first and second shut-off valves being interlocked such that, when said first shut-off valve is opened, said shut-off valve is closed, a source of compressed air, a compressed air conduit connected to said sourced of compressed air for directing air onto said tube in the vicinity of said amalgam-forming body for cooling said amalgam-forming body, a fourth shut-off valve disposed in said compressed air conduit, a third flow resistance disposed in said compressed air outlet adjacent said fourth shut-off valve, a rinsing conduit branched off from said compressed air conduit between said fourth shut-off valve and said third flow resistance, an outlet conduit connecting said rinsing conduit between said reaction vessel and said washing bottle adjacent to said washing bottle, a fifth shut-off valve connecting said outlet conduit and said washing bottle to atmosphere adjacent to said reaction vessel, said fifth shut-off valve controlled such that it opens together with said fourth shut-off valve.

3. An apparatus as set forth in claim 2, wherein said fifth shut-off valve is pneumatically controlled, and a control conduit branches off from said compressed air conduit behind said fourth shut-off valve for controlling the opening of said fifth shut-off valve.

* * * * *